United States Patent
Bandhauer et al.

(10) Patent No.: US 8,414,534 B2
(45) Date of Patent: Apr. 9, 2013

(54) HOLDING TANK DEVICES, SYSTEMS, AND METHODS FOR SURGICAL FLUIDICS CASSETTE

(75) Inventors: Mark H. Bandhauer, Orange, CA (US); John I. Muri, Aliso Viejo, CA (US); David King, Pleasanton, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 605 days.

(21) Appl. No.: 11/558,434

(22) Filed: Nov. 9, 2006

(65) Prior Publication Data

US 2008/0114301 A1     May 15, 2008

(51) Int. Cl.
   *A61M 1/00*        (2006.01)
   *A61M 37/00*      (2006.01)
   *F04B 43/08*       (2006.01)

(52) U.S. Cl. .......... 604/151; 604/540; 604/131; 604/28; 417/477.2

(58) Field of Classification Search .................. 604/153, 604/151

See application file for complete search history.

(56) References Cited

U.S. PATENT DOCUMENTS

| | | |
|---|---|---|
| 1,848,024 A | 3/1932 | Owen |
| 3,116,697 A | 1/1964 | Bilichniansky |
| 3,781,142 A | 12/1973 | Zweig |
| 4,189,286 A | 2/1980 | Murry et al. |
| 4,193,004 A | 3/1980 | Lobdell et al. |

(Continued)

FOREIGN PATENT DOCUMENTS

| | | |
|---|---|---|
| EP | 56019 A1 | 7/1982 |
| EP | 1010437 A1 | 6/2000 |

(Continued)

OTHER PUBLICATIONS

Phacoemulsification. Oct. 12, 2006. Wikipedia.com. Jun. 19, 2009 <http://en.wikipedia.org/wiki/Phacoemulsification>.*

(Continued)

*Primary Examiner* — Nicholas Lucchesi
*Assistant Examiner* — Weng Lee
(74) *Attorney, Agent, or Firm* — Abbott Medical Optics Inc.

(57) ABSTRACT

The present invention is generally directed to improved methods, devices, and systems for eye surgery. In some embodiments, the invention may provide new and/or improved devices, systems, and methods for detecting surgical fluids in a fluidics cassette, particularly cassettes which are used to couple an eye treatment probe to an eye treatment console. Rather than relaying on internal reflection by a gas-liquid interface, the fluid detection techniques described herein may make use of the changes in propagation of light through a portion of the holding tank when the portion varies between empty and full. For example, light may propagate directly through the holding tank portion when there is no surgical fluid, but may be directed away from a light detector when the portion of the holding tank is filled with surgical fluid. As the light may be controllably refracted using the interface between the transparent holding tank material and the surgical fluid, the propagation properties of the light may be more reliably predicted and controlled. While the sensor may not determine the actual liquid level within the holding tank, a plurality of individual liquid detectors may be sufficient to determine when it is appropriate to (for example) turn drain pumps on and off, when the holding tank is in danger of being overfilled, and the like. Other aspects of the invention may provide devices, systems, and methods for producing different types of fluidics cassette using a single cassette body type.

19 Claims, 11 Drawing Sheets

U.S. PATENT DOCUMENTS

| | | | |
|---|---|---|---|
| 4,564,342 A | 1/1986 | Weber et al. | |
| 4,773,897 A | 9/1988 | Scheller et al. | |
| 4,920,336 A | 4/1990 | Meijer | |
| 4,983,901 A | 1/1991 | Lehmer | |
| 5,006,110 A * | 4/1991 | Garrison et al. | 604/65 |
| 5,125,891 A | 6/1992 | Hossain et al. | |
| 5,195,960 A | 3/1993 | Hossain et al. | |
| 5,195,961 A | 3/1993 | Takahashi et al. | |
| 5,195,971 A | 3/1993 | Sirhan | |
| 5,230,614 A | 7/1993 | Zanger et al. | |
| 5,268,624 A | 12/1993 | Zanger | |
| 5,282,787 A | 2/1994 | Wortich | |
| 5,342,293 A | 8/1994 | Zanger | |
| 5,454,783 A | 10/1995 | Grieshaber et al. | |
| 5,470,211 A | 11/1995 | Knott et al. | |
| 5,520,652 A | 5/1996 | Peterson | |
| 5,549,461 A | 8/1996 | Newland | |
| 5,591,127 A | 1/1997 | Barwick, Jr. et al. | |
| 5,657,000 A | 8/1997 | Ellingboe | |
| 5,676,530 A | 10/1997 | Nazarifar | |
| 5,676,650 A | 10/1997 | Grieshaber et al. | |
| 5,693,020 A | 12/1997 | Rauh | |
| 5,700,240 A | 12/1997 | Barwick, Jr. et al. | |
| 5,733,256 A | 3/1998 | Costin | |
| 5,747,824 A * | 5/1998 | Jung et al. | 250/577 |
| 5,830,176 A | 11/1998 | MacKool | |
| 5,899,674 A | 5/1999 | Jung et al. | |
| 5,928,257 A | 7/1999 | Kablik et al. | |
| 6,024,428 A * | 2/2000 | Uchikata | 347/7 |
| 6,062,829 A | 5/2000 | Ognier | |
| 6,086,598 A | 7/2000 | Appelbaum et al. | |
| 6,117,126 A | 9/2000 | Appelbaum et al. | |
| 6,150,623 A | 11/2000 | Chen | |
| 6,179,829 B1 | 1/2001 | Bisch et al. | |
| 6,260,434 B1 | 7/2001 | Holtorf | |
| 6,360,630 B2 | 3/2002 | Holtorf | |
| 6,436,072 B1 | 8/2002 | Kullas et al. | |
| 6,452,120 B1 | 9/2002 | Chen | |
| 6,452,123 B1 | 9/2002 | Chen | |
| 6,491,661 B1 | 12/2002 | Boukhny et al. | |
| 6,511,454 B1 | 1/2003 | Nakao et al. | |
| 6,632,214 B2 | 10/2003 | Morgan et al. | |
| 6,674,030 B2 | 1/2004 | Chen et al. | |
| 6,962,488 B2 | 11/2005 | Davis et al. | |
| 7,012,203 B2 | 3/2006 | Hanson et al. | |
| 7,070,578 B2 | 7/2006 | Leukanech et al. | |
| 7,169,123 B2 | 1/2007 | Kadziauskas et al. | |
| 7,244,240 B2 | 7/2007 | Nazarifar et al. | |
| 7,300,264 B2 | 11/2007 | Souza | |
| 2001/0051788 A1 * | 12/2001 | Paukovits et al. | 604/67 |
| 2002/0019607 A1 | 2/2002 | Bui | |
| 2003/0073980 A1 | 4/2003 | Finlay et al. | |
| 2003/0108429 A1 * | 6/2003 | Angelini et al. | 417/3 |
| 2004/0037724 A1 | 2/2004 | Haser et al. | |
| 2005/0054971 A1 | 3/2005 | Steen et al. | |
| 2005/0069419 A1 | 3/2005 | Cull et al. | |
| 2005/0070859 A1 | 3/2005 | Cull et al. | |
| 2005/0118048 A1 | 6/2005 | Traxinger | |
| 2005/0245888 A1 | 11/2005 | Cull | |
| 2006/0145540 A1 | 7/2006 | Mezhinsky | |
| 2006/0219049 A1 | 10/2006 | Horvath et al. | |
| 2006/0219962 A1 * | 10/2006 | Dancs et al. | 250/577 |
| 2007/0016174 A1 | 1/2007 | Millman et al. | |
| 2007/0049898 A1 * | 3/2007 | Hopkins et al. | 604/403 |
| 2008/0033342 A1 | 2/2008 | Staggs | |
| 2008/0066542 A1 * | 3/2008 | Gao | 73/290 R |
| 2008/0112828 A1 | 5/2008 | Muri et al. | |
| 2008/0114289 A1 | 5/2008 | Muri et al. | |
| 2008/0114290 A1 | 5/2008 | King et al. | |
| 2008/0114291 A1 | 5/2008 | Muri et al. | |
| 2008/0114300 A1 | 5/2008 | Muri et al. | |
| 2008/0114311 A1 | 5/2008 | Muri et al. | |
| 2008/0114312 A1 | 5/2008 | Muri et al. | |
| 2008/0114372 A1 | 5/2008 | Edwards et al. | |
| 2008/0114387 A1 | 5/2008 | Hertweck et al. | |
| 2008/0125698 A1 | 5/2008 | Gerg et al. | |

FOREIGN PATENT DOCUMENTS

| | | |
|---|---|---|
| EP | 1310267 | 5/2003 |
| EP | 1704839 A1 | 9/2006 |
| EP | 1787606 A1 | 5/2007 |
| EP | 1873501 A1 | 1/2008 |
| EP | 1900347 A1 | 3/2008 |
| EP | 1867349 | 11/2008 |
| GB | 2230301 A | 10/1990 |
| WO | WO 93/17729 | 9/1993 |
| WO | WO 93/24082 | 12/1993 |
| WO | WO-9632144 A1 | 10/1996 |
| WO | WO 98/18507 | 5/1998 |
| WO | WO 99/17818 | 4/1999 |
| WO | WO-0070225 A1 | 11/2000 |
| WO | WO 02/34314 A1 | 5/2002 |
| WO | WO 2005/084728 | 9/2005 |
| WO | WO-2005092023 A2 | 10/2005 |
| WO | WO 2007/143677 A2 | 12/2007 |
| WO | WO-2008060859 A1 | 5/2008 |
| WO | WO-2008060902 A1 | 5/2008 |

OTHER PUBLICATIONS

"Phacoemulsification. Oct. 12, 2006. Wikipedia.com. Jun. 19, 2009 http://en.wikipedia.org/wiki/Phacoemulsification,".

* cited by examiner

HOLDING TANK DEVICES, SYSTEMS, AND METHODS FOR SURGICAL FLUIDICS CASSETTE

BACKGROUND OF THE INVENTION

The present invention is generally related to methods, devices, and systems for controlling surgical fluid flows, particularly during treatment of an eye.

The optical elements of the eye include both a cornea (at the front of the eye) and a lens within the eye. The lens and cornea work together to focus light onto the retina at the back of the eye. The lens also changes in shape, adjusting the focus of the eye to vary between viewing near objects and far objects. The lens is found just behind the pupil, and within a capsular bag. This capsular bag is a thin, relatively delicate structure which separates the eye into anterior and posterior chambers.

With age, clouding of the lens or cataracts are fairly common. Cataracts may form in the hard central nucleus of the lens, in the softer peripheral cortical portion of the lens, or at the back of the lens near the capsular bag.

Cataracts can be treated by the replacement of the cloudy lens with an artificial lens. Phacoemulsification systems often use ultrasound energy to fragment the lens and aspirate the lens material from within the capsular bag. This may allow the capsular bag to be used for positioning of the artificial lens, and maintains the separation between the anterior portion of the eye and the vitreous humour in the posterior chamber of the eye.

During cataract surgery and other therapies of the eye, accurate control over the volume of fluid within the eye is highly beneficial. For example, while ultrasound energy breaks up the lens and allows it to be drawn into a treatment probe with an aspiration flow, a corresponding irrigation flow may be introduced into the eye so that the total volume of fluid in the eye does not change excessively. If the total volume of fluid in the eye is allowed to get too low at any time during the procedure, the eye may collapse and cause significant tissue damage. Similarly, excessive pressure within the eye may strain and injure tissues of the eye.

While a variety of specific fluid transport mechanisms have been used in phacoemulsification and other treatment systems for the eyes, aspiration flow systems can generally be classified in two categories: 1) volumetric-based aspiration flow systems using positive displacement pumps; and 2) vacuum-based aspiration systems using a vacuum source, typically applied to the aspiration flow through an air-liquid interface. These two categories of aspiration flow systems each have unique characteristics that render one more suitable for some procedures than the other, and vice versa.

Among positive displacement aspiration systems, peristaltic pumps (which use rotating rollers that press against a flexible tubing to induce flow) are commonly employed. Such pumps provide accurate control over the flow volume. The pressure of the flow, however, is less accurately controlled and the variations in vacuum may result in the feel or traction of the handpiece varying during a procedure. Peristaltic and other displacement pump systems may also be somewhat slow.

Vacuum-based aspiration systems provide accurate control over the fluid pressure within the eye, particularly when combined with gravity-fed irrigation systems. While vacuum-based systems can result in excessive fluid flows in some circumstances, they provide advantages, for example, when removing a relatively large quantity of the viscous vitreous humour from the posterior chamber of the eye. However, Venturi pumps and other vacuum-based aspiration flow systems are subject to pressure surges during occlusion of the treatment probe, and such pressure surges may decrease the surgeon's control over the eye treatment procedure.

Different tissues may be aspirated from the anterior chamber of the eye with the two different types of aspiration flow. For example, vacuum-induced aspiration flow may quickly aspirate tissues at a significant distance from a delicate structure of the eye (such as the capsular bag), while tissues that are closer to the capsular bag are aspirated more methodically using displacement-induced flows.

Conventionally, fluid aspiration systems include a console and a fluidic cassette mounted on the console. The fluidic cassette is changed for each patient and cooperates with the console to provide fluid aspiration. Generally, a single type of cassette is used by a particular console, regardless of whether the procedure will require positive displacement aspiration, vacuum-based aspiration, or both.

In light of the above, it would be advantageous to provide improved devices, systems, and methods for eye surgery. It would be particularly advantageous if these improvements allowed a console to be used interchangeably with different types of cassettes tailored to the type of procedure which may be performed on a particular patient. It would also be advantageous to facilitate communication between the console and the fluidic network elements of the cassette regardless of the particular type of cassette mounted to the console for a particular procedure. When making use of a vacuum-induced aspiration flow network of a cassette, it might also be advantageous to detect the presence of fluid in a holding tank or the like, regardless of any motion or disruption of the liquid/gas interface within the tank. Improved devices, systems, and methods relating to fluidics cassettes for ocular surgical systems having different types of aspiration drive mechanisms may also be desirable.

BRIEF SUMMARY OF THE INVENTION

The present invention is generally directed to improved methods, devices, and systems for eye surgery. In some embodiments, the invention may provide new and/or improved devices, systems, and methods for detecting surgical fluids in a fluidics cassette, particularly cassettes which are used to couple an eye treatment probe to an eye treatment console. Rather than relaying on internal reflection by a gas-liquid interface, the fluid detection techniques described herein may make use of the changes in propagation of light through a portion of the holding tank when the portion varies between empty and full. For example, light may propagate directly through the holding tank portion when there is no surgical fluid, but may be directed away from a light detector when the portion of the holding tank is filled with surgical fluid. As the light may be controllably refracted using the interface between the transparent holding tank material and the surgical fluid (rather than the free surface or top of the surgical fluid within the holding tank, for example, as in U.S. Pat. No. 5,747,824, herein incorporated by reference), the propagation properties of the light may be more reliably predicted and controlled. While the sensor may not determine the actual liquid level within the holding tank, a plurality of individual liquid detectors may be sufficient to determine when it is appropriate to (for example) turn drain pumps on and off, when the holding tank is in danger of being overfilled, and the like. Other aspects of the invention may provide devices, systems, and methods for producing different types of fluidics cassette using a single cassette body type.

In a first aspect, the invention provides a surgical system comprising an eye treatment probe having a fluid aspiration port. An eye treatment console has a fluid detector system and a fluid aspiration drive system. The fluid detector system may include a visible or infrared emitter and a receiver. A cassette may include a surgical fluid aspiration system configured to couple the aspiration drive of the console to the aspiration port of the probe. The aspiration system may also have a fluid container including a first wall and a second wall with a volume portion therebetween. The first and second walls can be configured so that, when the cassette is mounted to the console and light is directed to the first wall from the emitter, the light either defines a first signal at the detector (when a given volume portion of the fluid container is filled with surgical fluid) or the light defines a second signal at the detector (when no surgical fluid is disposed in the volume portion).

The emitter may direct the light along a light path, with the first wall often being disposed at a first angle relative to the path. The second wall may be disposed at a second angle relative to the path. The fluid tank can be configured so that when no surgical fluid is disposed in the volume portion, the light is directed to the detector in an amount sufficient to produce the second signal. In contrast, when surgical fluid is disposed in the volume portion, light is reflected away from the detector so that a reduction, absence, or near absence of the light at the detector defines the first signal. In some embodiments, when surgical fluid is disposed within the surgical fluid path, the light from the emitter may be directed to the second wall at a sufficient angle that at least some of the light is reflected by the second wall and generally away from the receiver.

In another aspect, the invention provides a surgical cassette for use with an eye treatment system. The eye treatment system includes an eye treatment probe having a fluid aspiration port, along with an eye treatment console having a fluid detector system and a fluid aspiration drive system. The fluid detector system of the console may include a light emitter and a light signal receiver. The cassette comprises a surgical fluid aspiration system configured to couple the aspiration drive of the console to the aspiration port of the probe. The aspiration system may include a fluid container having a first wall and a second wall with a volume therebetween. The first and second walls may be configured so that, when the cassette is mounted to the console and light is directed to the first wall from the emitter: the light defines a first signal at the detector when the volume is filled with surgical fluid; and the light defines a second signal at the detector when no surgical fluid is disposed in the volume.

In another aspect, the invention provides an eye treatment method comprising aspirating surgical fluid from an eye through an aspiration port of an eye treatment probe. The aspiration of the surgical fluid is driven with a drive system of an eye treatment console. The drive system is coupled to the probe by a cassette having a fluid container. The drive system of the console is operated in response to first and second signals. The first signal is generated by transmitting light toward the first wall when a given volume portion of the container is filled with surgical fluid. The second signal is generated by transmitting light toward the first wall when there is no surgical fluid disposed in the volume portion.

In another aspect, the invention provides an eye surgery system comprising a console having a cassette receptacle, a volumetric pump drive, and a vacuum source. First and second cassette bodies are each configured for mounting to the receptacle of the console, with each having surfaces for supporting a holding tank. A first aspiration fluid network is mounted to the first cassette body so as to define a first cassette type. The first aspiration fluid network is configured to drive aspiration fluid to a waste container or bag using the volumetric pump drive without coupling the vacuum source to any holding tank of the cassette when the first cassette body is received by the receptacle. A second aspiration fluid network is mounted to the second cassette body so as to define a second cassette type. The second aspiration fluid network includes a holding tank that is mounted to the support surfaces of the second cassette body. The second aspiration fluid network is configured to draw aspiration fluid into the holding tank by coupling the holding tank with the vacuum source of the console when the cassette body is received by the receptacle.

In another aspect, the invention provides an eye surgical cassette for use in an eye surgery system. The eye surgery system comprises a probe having an aspiration port and a console. The console has a cassette receptacle, a volumetric pump drive, and a vacuum source. The system also includes a first cassette type including a cassette body configured for mounting to the receptacle of the console. The cassette body also has surfaces for supporting a holding tank. A first aspiration fluid network is mounted to the first cassette body, with the first aspiration fluid network including a holding tank mounted to the support surfaces. The first aspiration fluid network is configured to draw aspiration fluid into the holding tank by coupling the holding tank with the vacuum source of the console when the first cassette body is received by the receptacle. The cassette comprises a second cassette body configured for mounting to the receptacle of the console. While the second cassette body also has surfaces for supporting a holding tank, the second aspiration fluid network that is mounted to the second cassette body is configured to drive aspiration fluid to a waste container or bag using the volumetric pump drive and without coupling the vacuum source of the console to any holding tank of the cassette when the cassette body is received by the receptacle.

In another aspect, the invention provides a method for producing first and second cassette types for use in an eye surgery system. The system includes a console having a cassette receptacle, a volumetric pump drive, and a vacuum source. The method comprises providing first and second cassette bodies, each body configured for mounting to the receptacle of the console and having surfaces for supporting a holding tank. A first aspiration fluid network is mounted to the first cassette body. The first network is configured to drive aspiration fluid using the volumetric pump drive without coupling the vacuum source of the console to any holding tank. A second aspiration fluid network is mounted to the second cassette body. The second aspiration fluid network includes a holding tank that is mounted to the support surfaces of the second cassette body. Hence, the second aspiration fluid network can be configured to draw aspiration fluid into the holding tank by coupling of the holding tank with the vacuum source of the console when its second cassette body is received by the receptacle.

BRIEF DESCRIPTION OF THE DRAWINGS

FIGS. 9(a) and 9(b) schematically illustrate changes in refraction and/or reflection of the light from an illumination source through a portion of a volume of a holding tank when the volume portion is empty (FIG. 9(a)) or filled with liquid (FIG. 9(b)), thereby allowing detection of the presence of surgical fluid within an associated portion of a surgical fluid holding tank of a fluidic cassette or the like.

DETAILED DESCRIPTION OF THE INVENTION

Figure 1:
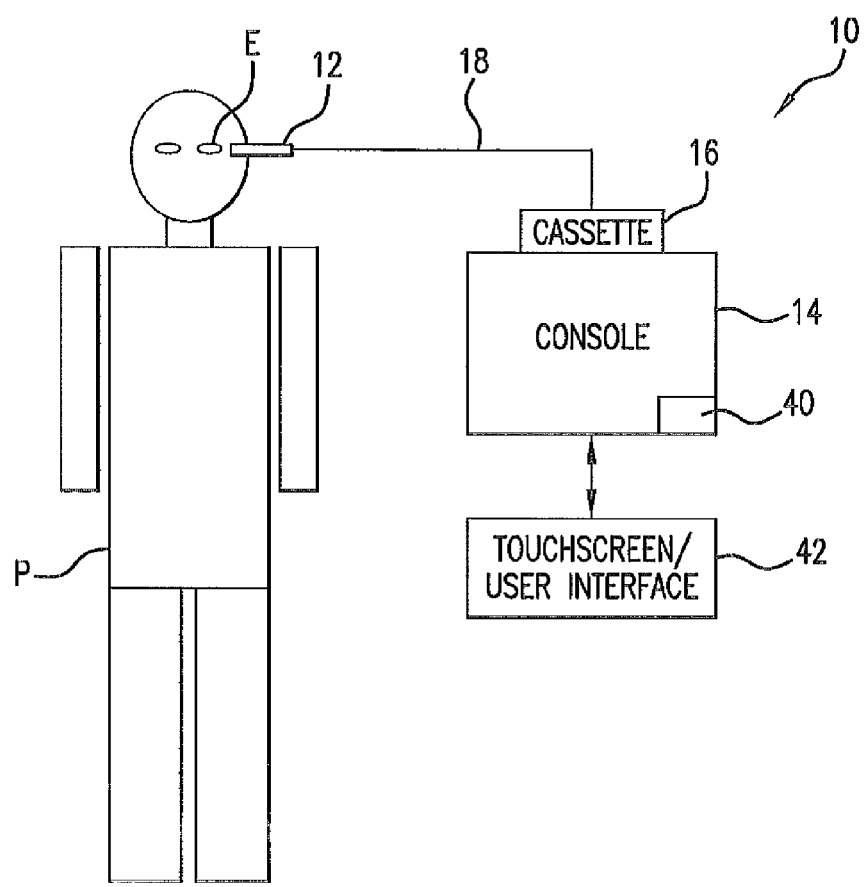
FIG. 1 schematically illustrates an eye treatment system in which a cassette couples an eye treatment probe with an eye treatment console, along with a method for use of the system for treating the eye of a patient.

The present invention generally provides improved devices, systems, and methods for treating an eye of the patient.

Embodiments of the present invention may include eye surgery consoles that are coupled to eye treatment probes using one or more types of fluidic cassettes. At least one type of cassette may include an intermediate fluid holding tank, which may often find use during procedures which involve vacuum-induced aspiration of fluid from an eye of the patient. The level of surgical fluids within such a holding tank may be maintained to within pre-determined limits in order to ensure proper operation of the system. Embodiments of the invention may provide devices, systems, and methods for detecting surgical fluids within the holding tank.

Exemplary embodiments of the surgical fluid detection systems described herein may make use of an emitter such as a light-emitting diode, a diode laser, or the like. The light from the light emitter may be directed to walls of the holding tank which are transparent to the light, with the walls often being disposed at an angle relative to the incident light. Generally, light from the emitter is incident on a first wall, enters a volume inside the tank, and then exits a second wall. Some portion of the light from the emitter may then ultimately be received by a detector, the amount of light received (or absence or reduction thereof) depending upon the presence or absence of surgical fluid within a portion of the volume through which the light may pass. When no fluid is present in the volume portion within the tank, at least a portion of the light from the emitter may pass into and out of the tank with limited (or even no) net refractive bending of the light. Under these conditions, a predetermined portion of the light may directly enter into a detector, thus indicating that no fluid is present in the volume portion (i.e., in the volume of the tank that is at or near the level of the light detection system). When fluid rises to the level of the emitter/detector pair, the light may be refracted at the boundaries between the walls and the volume portion in a way that all or substantially all the light is either refracted away from the detector by the second wall and/or is reflected by the second wall. In either case, less of the light, substantially no light, or even none of the light from the emitter may be directed to or sensed by the detector when fluid is present.

Alternatively, surgical fluid detection system may be configured such that when no fluid is present in the volume portion, the light, or at least most of the light, may be directed away from the detector, by refraction and/or reflection, thus indicating that no fluid is present at the level of the light detection system. In such embodiments, when the fluid rises to the level of the emitter/detector pair, a predetermined portion of the light is directed to the detector.

Advantageously, the signal at the detector depends only on the presence or absence of surgical liquid, and is independent of the quality or characteristics of the liquid or the liquid/air interface within the tank. Furthermore, independent design parameters can be selected based on, for example, the characteristics of diode and/or detector included in the system. Some of these design parameters may include the refractive index of the wall material and the angles of the wall where the beam enters and exits the tank, as well as the spacing between these two walls.

In some embodiments, a plurality of emitter/detector pairs may be placed at predetermined levels corresponding to different or substantially different volume portions of the holding tank. Each emitter/detector pair of the plurality may be used to detect differing total quantities of fluid in the holding tank, with the light emitter and detector of each pair typically being generally disposed at about the same tank level so that the light that passes therebetween is not angled relative to the fluid surface within the tank.

In certain embodiments, the surgical fluid detection system may be configured to include at least one threshold level that is selected such that a first output from the detector is generated when the amount of light from the emitter entering the detector is equal to or above the threshold level. The surgical fluid detection system may be further configured such that a second output is generated when the amount of light from the light emitter entering the detector is below the threshold level. The surgical fluid detection system may be configured such the first output indicates that fluid is not present in a given volume portion and the second output indicates that fluid is present in the volume portion. Alternatively, the surgical fluid detection system may be configured such the first output indicates that fluid is present in the volume portion and the second output indicates that fluid is not present in the volume portion.

Embodiments of the present invention include or make use of a fluid aspiration system having a console on which multiple types of interchangeable fluidic cassettes can be mounted. Each type of cassette may include components for enabling one or both of displacement-based and vacuum-based aspiration. The cassette may include a surgical fluid network, and mounting of the cassette to the console allows various network elements of the cassette to interface with corresponding components of the console. The fluid network of the cassette may include resiliently deformable tubing, a pressure sensor, a holding tank or chamber, and the like. The components of the fluid network may change depending on whether the cassette enables displacement-based or vacuum-based aspiration, or both. For example, in order to enable displacement-based aspiration, a cassette body may constrain a segment of the tubing in an arcuate configuration, so that when the cassette is mounted to the console a peristaltic drive rotor of the console engages the arc segment of tubing. This allows positive displacement pumping of aspiration fluid from the eye, through the probe, and into a waste receptacle. When vacuum-based aspiration is needed, the fluid network of the cassette may include a vacuum chamber drawing on a vacuum source within the console.

Referring to FIG. 1, a system 10 for treating an eye E of a patient P generally includes an eye treatment probe handpiece 12 coupled to a console 14 by a cassette 16 mounted on the console. Handpiece 12 generally includes a handle for manually manipulating and supporting an insertable probe tip. The probe tip has a distal end which is insertable into the eye, with one or more lumens in the probe tip allowing irrigation fluid to flow from the console 14 and/or cassette 16 into the eye. Aspiration fluid may also be withdrawn through a lumen of the probe tip, with the console 14 and cassette 16 generally including a vacuum aspiration source, a positive displacement aspiration pump, or both to help withdraw and control a flow of surgical fluids into and out of eye E. As the surgical fluids may include biological materials that should not be transferred between patients, cassette 16 will often comprise a disposable (or alternatively, sterilizable) structure, with the surgical fluids being e through flexible conduits 18 of the cassette that avoid direct contact in between those fluids and the components of console 14.

When a distal end of the probe tip of handpiece 12 is inserted into an eye E (for example) for removal of a lens of a patient with cataracts, an electrical conductor (not shown) may supply energy from console 14 to an ultrasound transmitter of the handpiece. Alternatively, the handpiece 12 may be configured as an I/A or vitrectomy handpiece. Also, the ultrasonic transmitter may be replaced by other means for emulsifying a lens, such as a high energy laser beam. The ultrasound energy from handpiece 12 helps to fragment the tissue of the lens, which can then be drawn into a port of the tip by aspiration flow. So as to balance the volume of material removed by the aspiration flow, an irrigation flow through handpiece 12 (or a separate probe structure) may also be provided, with both the aspiration and irrigations flows being controlled by console 14.

So as to avoid cross-contamination between patients without incurring excessive expenditures for each procedure, cassette 16 and its flexible conduit 18 may be disposable. Alternatively, the flexible conduit or tubing may be disposable, with the cassette body and/or other structures of the cassette being sterilizable. Regardless, the disposable components of the cassette are typically configured for use with a single patient, and may not be suitable for sterilization. The cassette will interface with reusable (and often quite expensive) components of console 14, including peristaltic pump rollers, a Venturi or other vacuum source, a controller 40, and the like.

Controller 40 may include an embedded microcontroller and/or many of the components of a personal computer, such as a processor, a data bus, a memory, input and/or output devices (including a touch screen user interface 42), and the like. Controller 40 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 40 may have (or be coupled to) a recording media reader, or the code may be transmitted to controller 40 by a network connection such as an internet, an intranet, an Ethernet™, a wireless network, or the like. Along with programming code, controller 40 may include stored data for implementing the methods described herein, and may generate and/or store data that records perimeters with corresponding to the treatment of one or more patients. Many components of console 14 may be found in or modified from known commercial phacoemulsification systems from Advanced Medical Optics Inc. of Santa Ana, Calif.; Alcon Manufacturing, Ltd. of Ft. Worth, Tex., Bausch and Lomb of Rochester, N.Y., and other suppliers.

Figure 2:
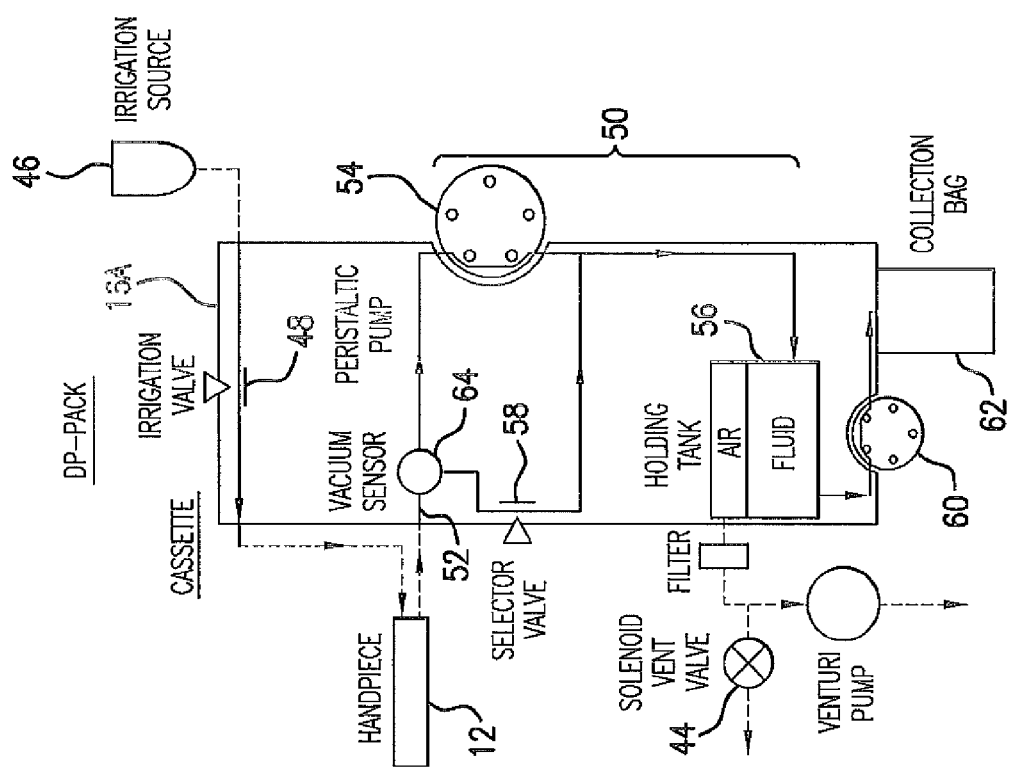
FIG. 2 schematically illustrates a dual mode cassette having a surgical fluid pathway network for use in the system of FIG. 1.

Referring now to FIGS. 1 and 2, components of the aspiration and irrigation fluid flow networks of system 10 are described in more detail with respect to a dual mode cassette 16A that enables both displacement-based and vacuum-based aspiration modes. FIG. 2 generally highlights the surgical aspiration and irrigation fluid control elements included within the cassette 16A, with the irrigation components often being relatively straightforward. An irrigation source 46 of the console optionally provides irrigation fluid pressure control by relying at least in part on a gravity pressure head that varies with a height of an irrigation fluid bag or the like. An irrigation on/off pinch valve 48 may generally include a short segment of a flexible conduit of cassette 16A, which can be engaged and actuated by an actuator of the console 14, with a surface of the cassette body often being disposed opposite the actuator to facilitate closure of the conduit lumen. Alternative irrigation flow systems may include positive displacement pumps, alternative fluid pressurization drive systems, fluid pressure or flow modulating valves, and/or the like. In certain embodiments, irrigation fluid is alternatively or additionally provided to a separate handpiece (not shown).

The aspiration flow network 50 generally provides an aspiration flow path 52 that can couple an aspiration port in the tip of handpiece 12 to either a peristaltic pump 54 and/or to a fluid container or holding tank 56. Fluid aspirated through the handpiece 12 may be contained in the holding tank 56 regardless of whether the aspiration flow is induced by peristaltic pump 54 or the vacuum applied to the holding tank 56. When valve 58 is closed and peristaltic pump 54 is in operation, pumping of the aspiration flow may generally be directed by the peristaltic pump 54, independent of the pressure in the holding tank 56. Conversely, when peristaltic pump 54 is off, flow through the peristaltic pump may be halted by pinching of the elastomeric tubing arc of the peristaltic pump by one or more of the individual rollers of the peristaltic pump rotor. Hence, any aspiration fluid drawn into the aspiration network when peristaltic pump 54 is off will typically be effected by opening of a selector control valve 58 so that the aspiration port of the probe is in fluid communication with the holding tank. Regardless, the pressure within tank 56 may be maintained at a controlled vacuum level, often at a fixed vacuum level, by a vacuum system 44 of the console. The vacuum system 44 may comprise a Venturi pump, a rotary vane pump, a vacuum source, or the like. Aspiration flow fluid held into holding tank 56 may be removed by a peristaltic drain pump 60 and directed to a disposal fluid collection bag 62. Vacuum pressure at the surgical handpiece may be maintained within a desired range through control of the fluid level in the holding tank.

In more detail, the operation of aspiration flow network 50 can be understood by first considering the flow when valve 58 is closed. In this mode, peristaltic pump 54 draws fluid directly from handpiece 12, with a positive displacement peristaltic pump flow rate being controlled by the system controller 40 (see FIG. 1). To determine the appropriate flow rate, the level of vacuum within the aspiration flow network may be identified in part with reference to a vacuum sensor 64 disposed along the aspiration flow network 50 between peristaltic pump 54 and handpiece 12. This allows the system to detect and adjust for temporary occlusions of the handpiece and the like. While the aspiration material flows through holding tank 56 and eventually into collection bag 62, the holding tank pressure may have little or no effect on the flow rate in this mode.

When peristaltic pump 54 is not in operation, rotation of the peristaltic pump is inhibited and the rotors of the peristaltic pump pinch the arcuate resilient tubing of the probe so as to block aspiration flow. Material may then be drawn into the aspiration port of handpiece 12 by opening selector valve 58 and engagement or operation of the vacuum system 44. When valve 58 is open, the aspiration port draws fluid therein based on the pressure differential between holding tank 56 and the chamber of the eye in which the fluid port is disposed, with the pressure differential being reduced by the total pressure loss of the aspiration flow along the aspiration path between the tank and port. Hence, aspiration network 50 of the dual mode cassette 16A allows system 10 to operate in either peristaltic or vacuum-based pumping modes.

Figure 3:
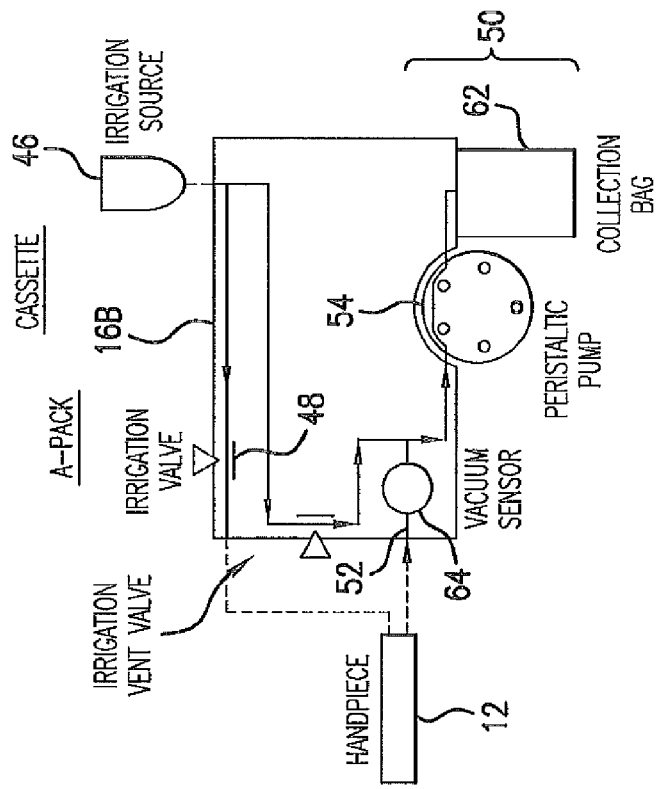
FIG. 3 schematically illustrates a single mode displacement-based aspiration cassette having a surgical fluid pathway network for use in the system of FIG. 1.

When only displacement-based pumping will be used for a particular procedure, an alternative cassette may be employed in the console 14, with the alternative cassette lacking a holding tank 56, selector valve 58, and the like. Referring now to FIGS. 1 and 3, components of a single mode cassette 16B are described, the single mode cassette enabling only the displacement-based aspiration mode. Within the single mode cassette, peristaltic pump 54 draws fluid directly from handpiece 12, with a positive displacement peristaltic pump flow rate being controlled by the system controller 40 (see FIG. 1). To determine the appropriate flow rate, the level of vacuum within the aspiration flow network may be identified in part with reference to a vacuum sensor 64 disposed along the aspiration flow network 50 between peristaltic pump 54 and handpiece 12. The aspiration material flows directly into collection bag 62. Alternatively, a single mode cassette may also be provided that only enables vacuum-based aspiration.

As a dual mode cassette may be somewhat more complex, a single mode cassette may be both simpler and less expensive. Therefore, the present invention may avoid complexity and provide cost savings by enabling the use of a less expensive single mode cassette when only a single aspiration mode is needed during a procedure on a particular patient.

Figure 4:
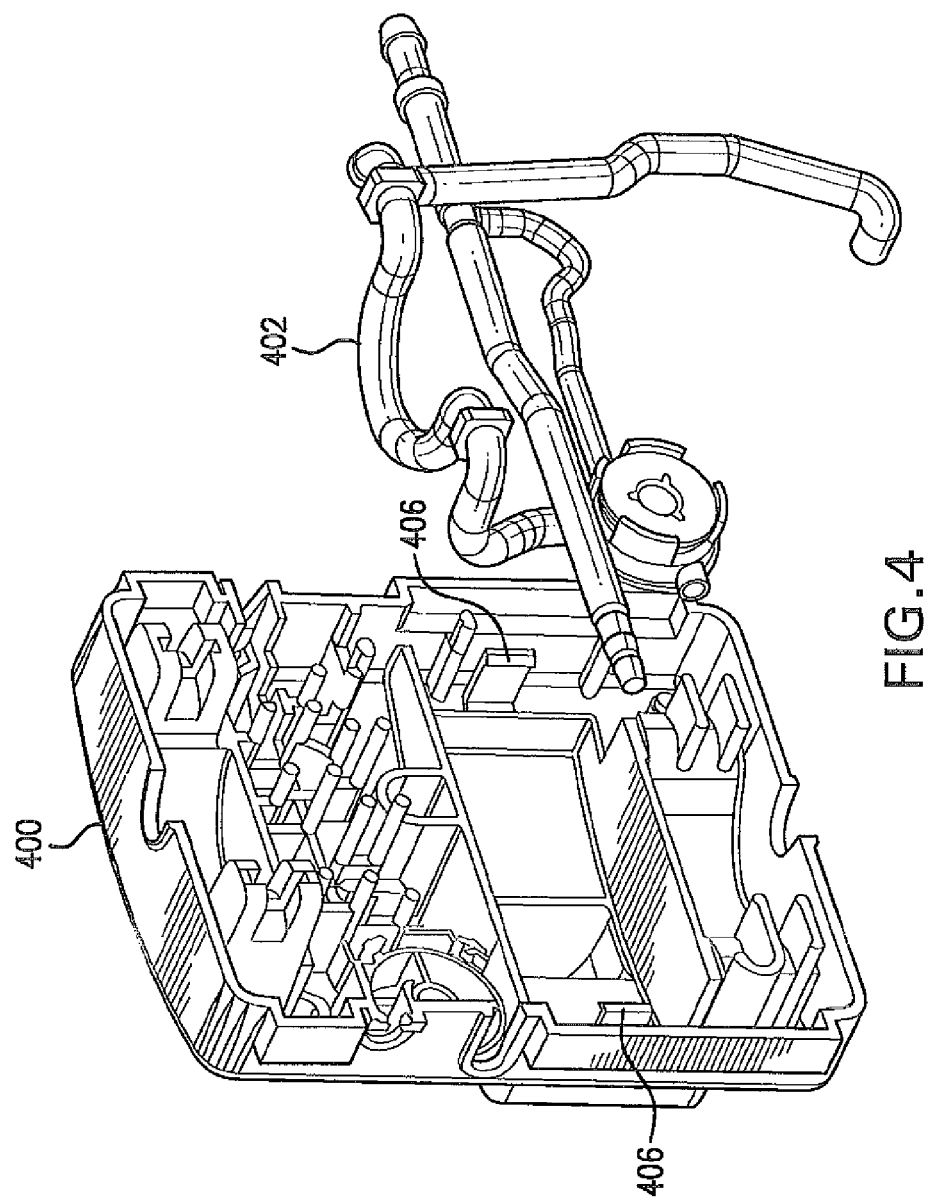
FIG. 4 is a perspective view showing a single mode fluid network that is mountable on a common cassette frame.
Figure 5:
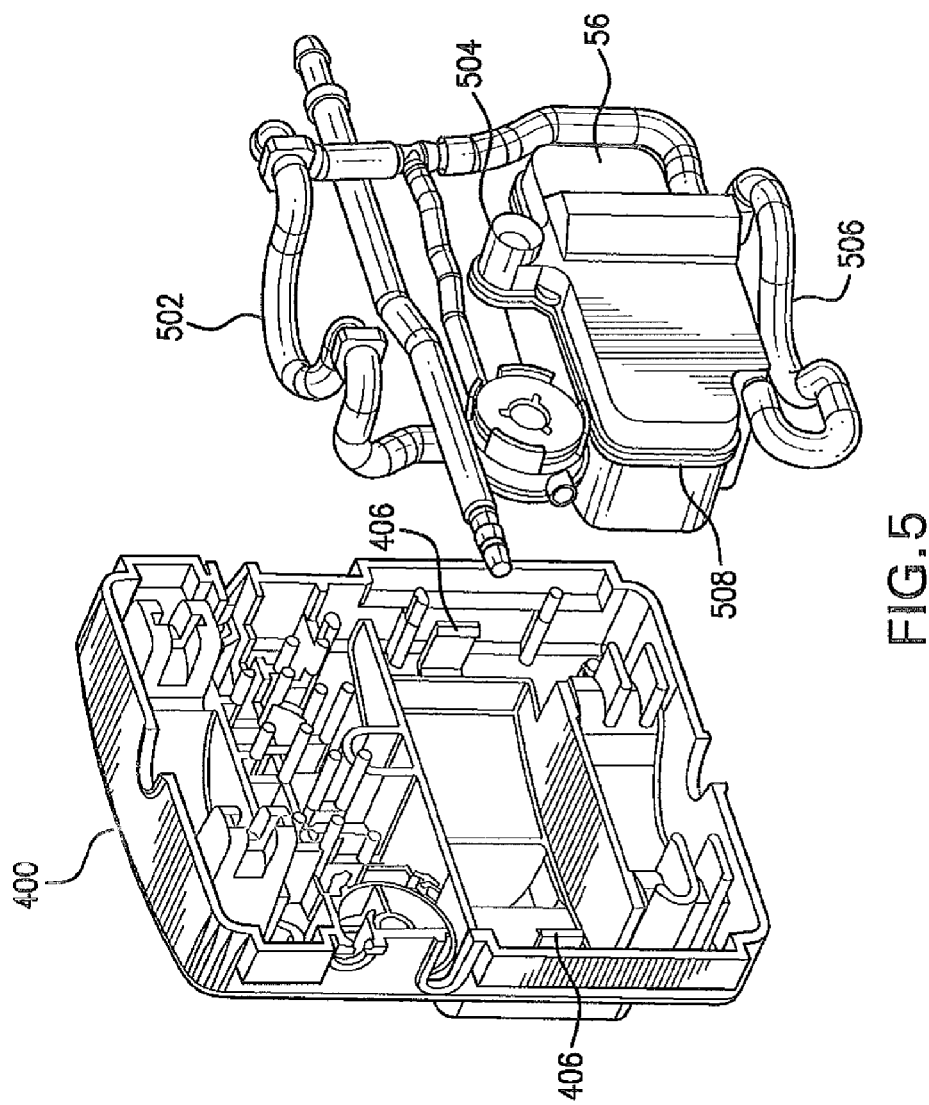
FIG. 5 is a perspective view showing a dual mode fluid network that is mountable on a common cassette frame.

In one embodiment of the present invention, fluid networks specialized for each different type of cassette (e.g., single mode or dual mode) can be interchangeably mounted within a common cassette frame. With reference to FIGS. 4 and 5, a single mode fluid network 402 (displacement mode only) and a dual mode fluid network 502 are both mountable on a common cassette frame 400. The common cassette frame 400 includes channels and receptacles for receiving and securing the fluid networks' tubing, valves, tanks, etc. The cassette frame and the fluid networks are cooperatively designed such that the cassette frame is capable of receiving multiple, differently configured fluid networks. By utilizing a common frame for multiple types of cassettes, the present invention may eliminate or reduce the excess production and inventory costs related to having multiple types of cassettes. The common frame 400 also makes it easier for the console to accept multiple types of cassettes, whereby at least the physical dimensions of the cassette frame remain the same amongst different types of cassettes.

As shown in FIG. 5, fluid network 502, which is a dual mode fluid network that enables vacuum-based aspiration, includes a holding tank 56 that is not present in fluid network 402. Tank 56 may be connected to a vacuum pump (e.g., a Venturi pump or a rotary vane pump) located in the surgical console and may provide vacuum-based aspiration to the handpiece when selector valve 58 (FIG. 2) connects the handpiece to the vacuum generated in tank 56. The holding tank may also receive aspirated fluids before the fluid is drained to the collection bag.

Still referring to FIGS. 4 and 5, holding tank 56 may be supported and received by holding tank support surfaces 406 of cassette frame or body 400, with the exemplary holding tank support surfaces comprising resiliently deflectable protruding tabs that snap onto a flange 508 of the holding tank. Note that the holding tank support surfaces 406 may be present in both forms of the cassette, although fluid network 402 of the displacement mode only cassette shown in FIG. 4 does not include a holding tank. Along with the snap in tabs, additional surfaces of the cassette frame 400 may engage and help position associated surfaces of the holding tank 56.

Figure 5A:
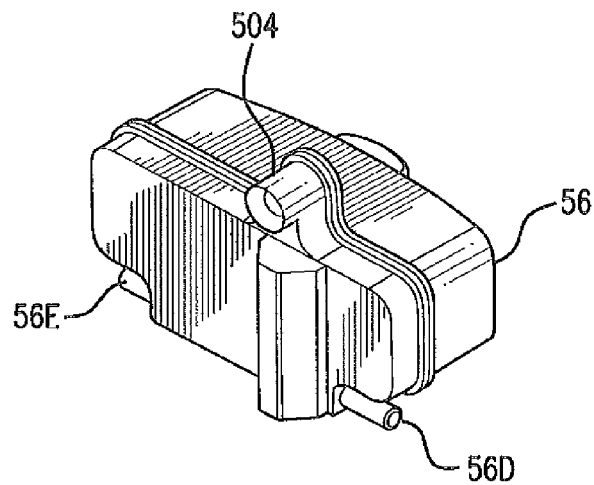
FIGS. 5(a)-(c) are perspective views of the holding tank of the dual mode fluid network of FIG. 5.
Figure 5B:
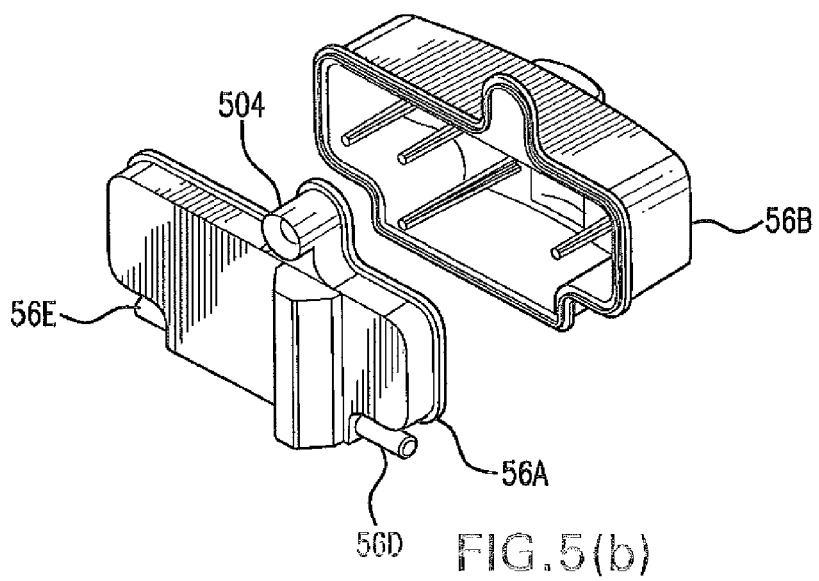
Figure 5C:
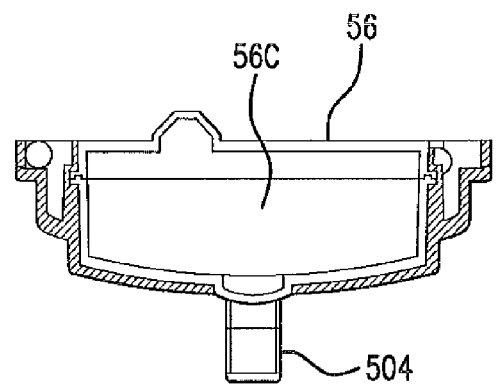

FIGS. 5(a)-(c) illustrate an exemplary holding tank 56 from dual mode fluid network 502. In particular, tank 56 may be formed from two clear plastic pieces 56A and 56B to define a hollow interior 56C therein. The tank may include a connecting stem 504 that communicates with hollow interior 56C and connects the tank to an exterior vacuum source (e.g., a vacuum pump located in the console). Tank 56 may also include connectors 56D and 56E, which allow the tank to be connected to the fluid network via tubing. For example, connector 56D may connect the holding tank (via the selector valve) to the handpiece 12 (FIG. 2). Vacuum suction may be provided to the handpiece through connector 56D and aspirated fluids may be received into the holding tank via this connector. Connector 56E may connect the holding tank to the collection bag 62 (FIG. 2). Tubing that leads from connector 56E to the collection bag may include an arcuate section 506 (FIG. 5) that enables displacement-based evacuation of the fluids in the holding tank when coupled with a peristaltic pump (e.g., pump 60 of FIG. 2).

Figure 7:
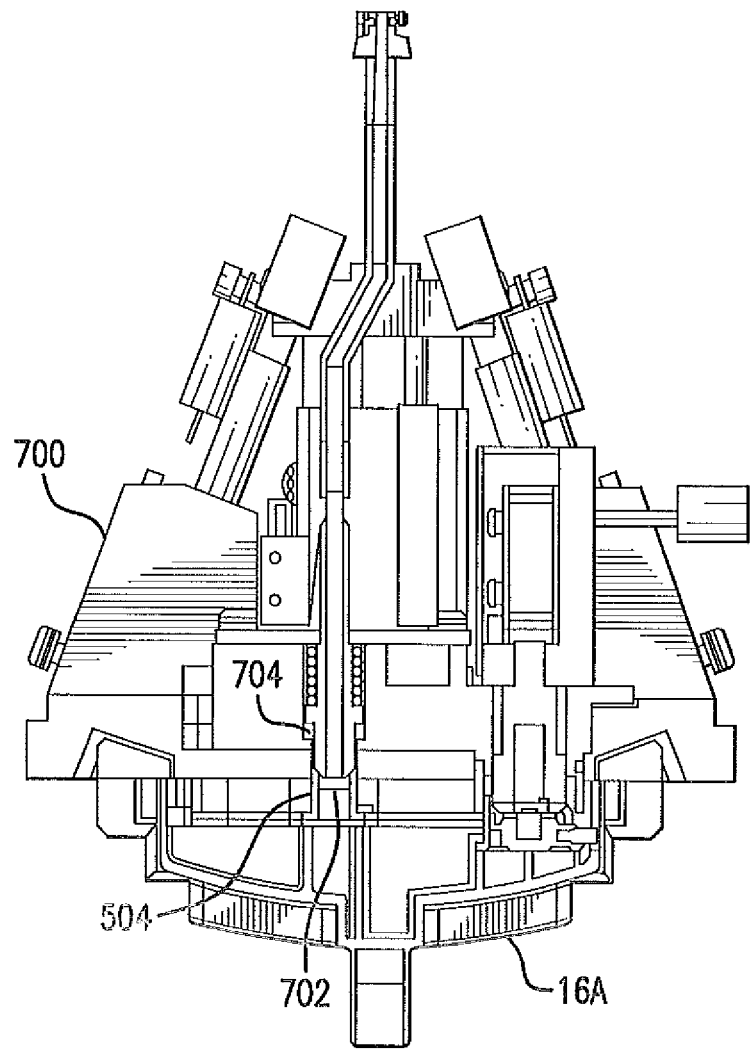
FIG. 7 is a plan view of a surgical console and cassette showing a microswitch used to provide a functional indicator of the eye treatment cassette.
Figure 7A:
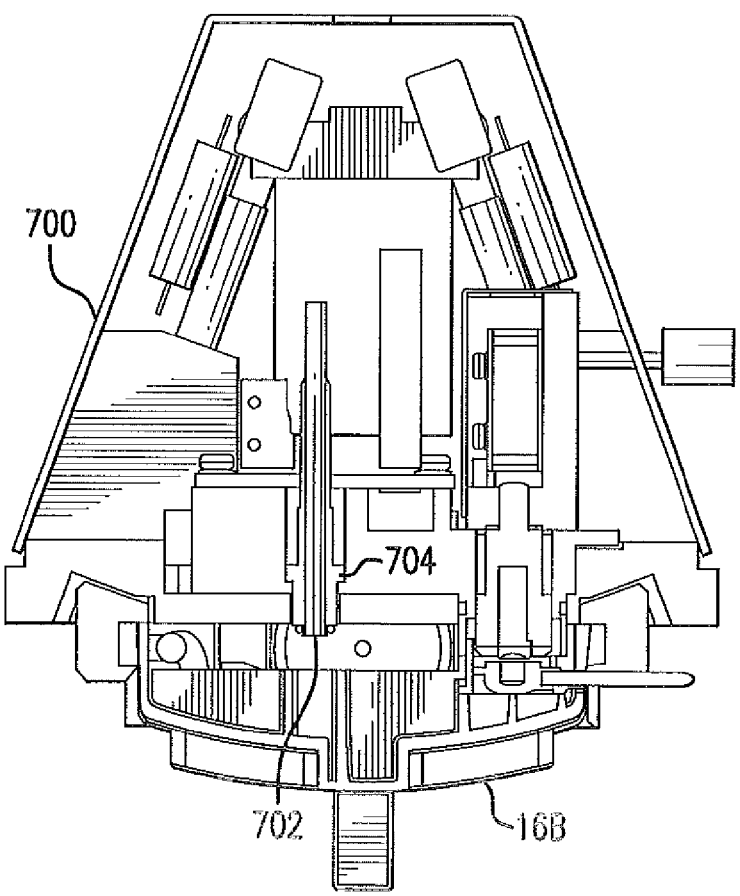
FIG. 7(a) is a plan view showing a position of the microswitch in the console when the installed eye treatment cassette does not have a functional indicator.

The console and the cassette may communicate to establish the functionality of the mounted cassette (i.e., the modes of aspiration enabled by the cassette). In one approach, a cassette may include a functional indicator that is detected by the console and which identifies the available functionalities of the installed cassette. For example, with reference to FIG. 5, fluid network 502 for a dual mode cassette includes a holding tank 56. Holding tank 56 may include a connecting stem 504, which connects the holding tank with a vacuum pump (not shown) located in the surgical console on which the dual mode cassette 16A is mounted. With reference to FIG. 7, engagement of the connecting stem 504 with a sealing nipple 702 of the surgical console 700 may actuate a microswitch 704 and indicate to the console that vacuum-enabled cassette 16A has been installed. In response, the console 700 may activate its vacuum pump and other necessary mechanism in preparation for vacuum-based aspiration. Conversely, as illustrated by FIG. 7(a), when cassette 16B (which only enables displacement-based aspiration) is installed on console 700, microswitch 704 is not triggered because no holding tank is installed in cassette 16B. Accordingly, the console will be informed that no vacuum-based aspiration is available with the mounted cassette. Therefore, utilizing a functional indicator, the surgical console may be informed upon mounting of the cassette that vacuum-based aspiration is available with the mounted cassette. In an embodiment where only two different cassettes are available (i.e., a displacement mode cassette and a dual mode cassette with vacuum aspiration), the console may confirm by presence of the holding tank which of the two types of cassettes has been mounted on the console.

It should be understood that the foregoing is but one illustrative method of communication between the console and the cassette to establish functionality of the installed cassette. Alternative methods and structures may also be used. For example, a non-mechanical method may be used where the cassette is labeled with a bar code containing functional information that is automatically scanned by the console. Regardless of the specific method used, the console and cassette of the present invention communicate to establish the functionalities available with the installed cassette, and the console prepares itself accordingly.

Figure 6:
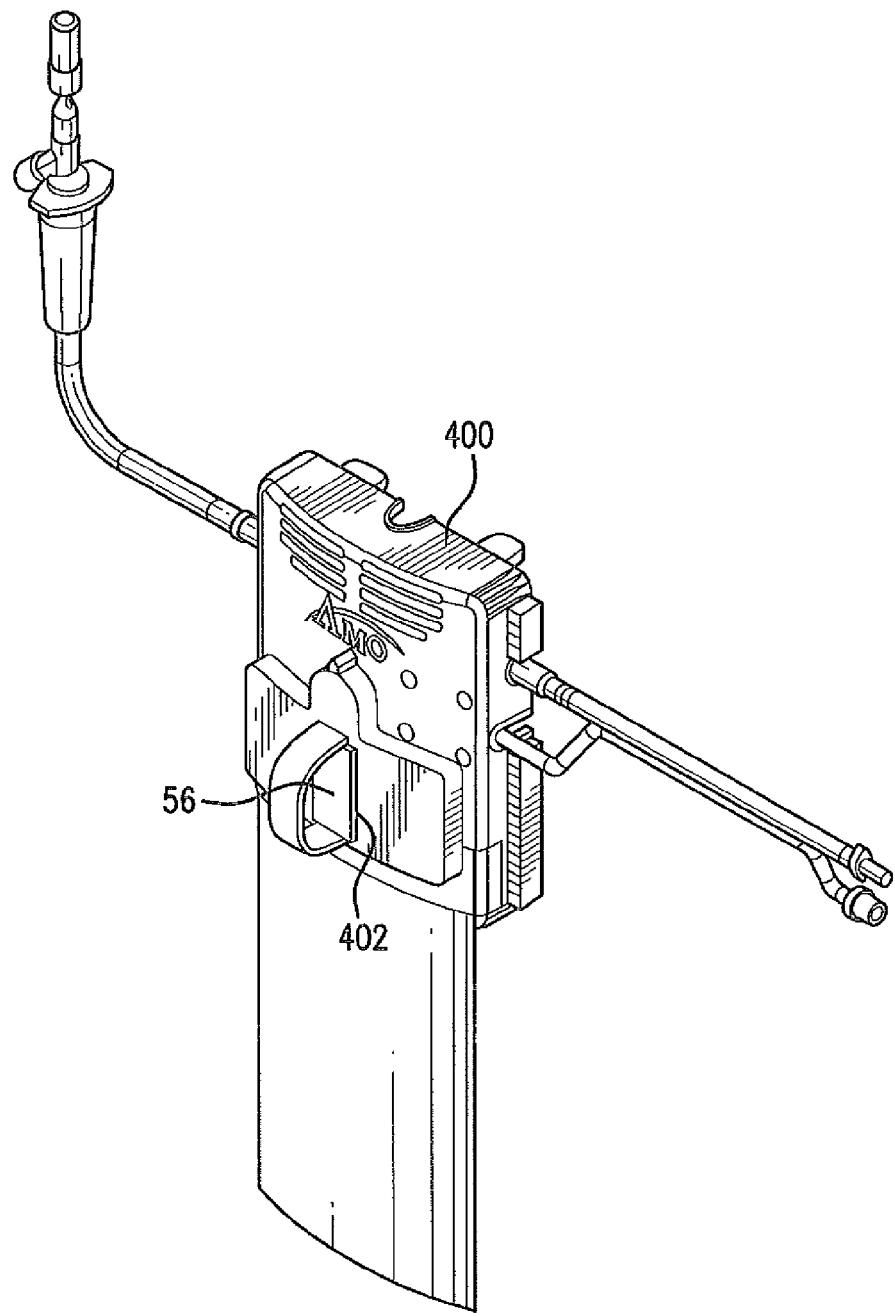
FIG. 6 is a perspective view showing an eye treatment cassette having a visual indication of its functionality.

The exemplary cassette may possess a visual indicator of its functionality (i.e., the aspiration modes enabled by the cassette). For example, with reference to FIG. 6, cassette frame 400 may include a window 404 through which the holding tank 56 of a dual mode fluid network may be seen. Therefore, if a holding tank is visible through window 402, a system operator will be informed that vacuum-based aspiration is available with the mounted cassette. In an embodiment where only two different cassettes are available (i.e., a displacement mode cassette and a dual mode cassette with vacuum aspiration), an operator may also visually confirm which of the two types of cassettes has been mounted on the console. Other visual indicia, such as alphanumeric codes or color-coded patches, may also be used to indicate the functionality of the cassette. In some embodiments, a clear cassette may be provided through which the presence of a holding tank may be visually confirmed and indicate the functionality of the cassette.

Figure 8:
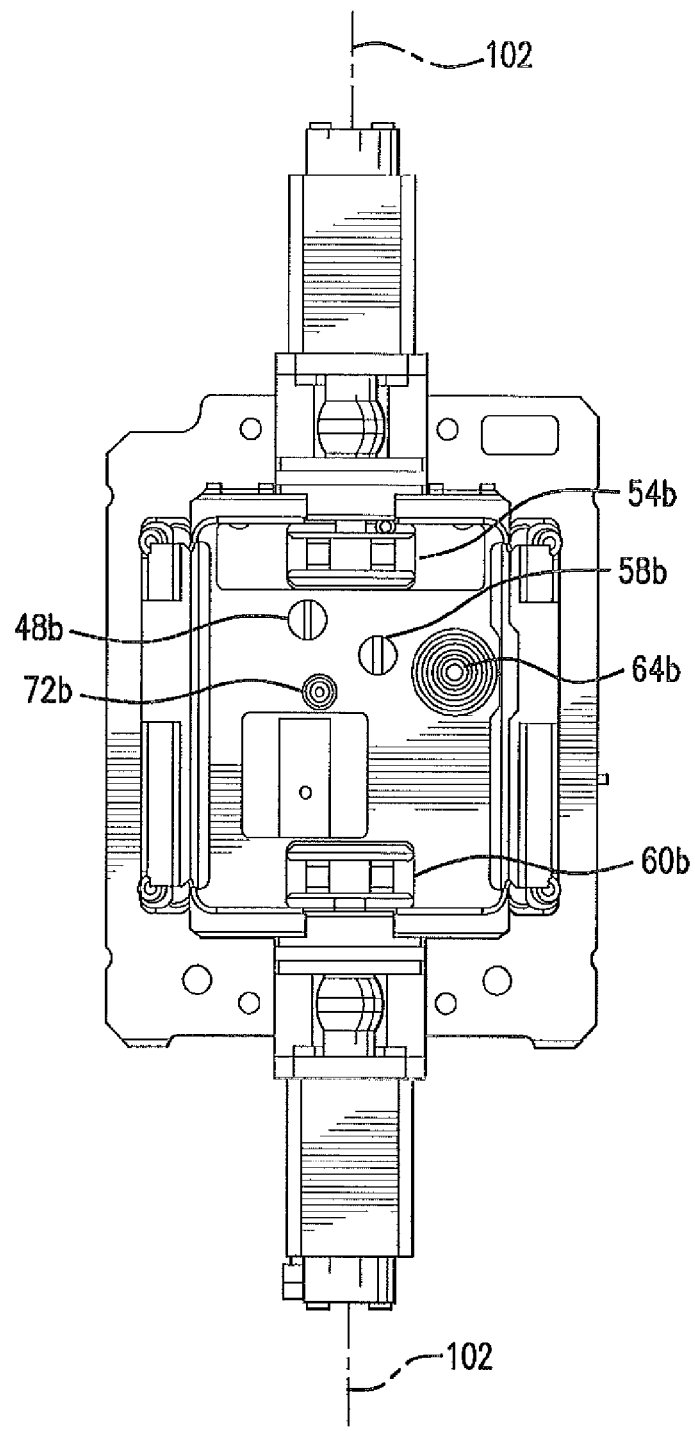
FIG. 8 is a plan view showing the coupling components of a console configured to receive multiple types of eye treatment cassettes.

FIG. 8 illustrates a surgical console according to the present invention which interchangeably receives multiple types of fluidic cassettes that enable one or both of displacement-based and vacuum-based aspiration modes. Engagement between the cassette and the cassette receptacle of console 14 can be understood with reference to FIGS. 2, 3, and 8. In particular, aspiration drive rotor 54b rotates about axis 102 and drives peristaltic pump 54 in either cassette 16A or 16B. Pressure receiver 64b and valve actuator 48b respectively couple with vacuum sensor 64 and irrigation valve 48 mounted in either type of cassette. When dual mode cassette 16A is mounted on the console, drain drive rotor 60 rotates about axis 102 to drive peristaltic drain pump 60 in the cassette. Valve actuator 58b is coupled with switching valve 58 of cassette 16A. Vacuum coupler 72b couples with holding tank 56 of cassette 16A. And, as previously described with respect to FIGS. 5 and 7, connecting stem 504 of holding tank 56 actuates a microswitch 704 within coupler 72b and indicates to the console that vacuum aspiration is available with the mounted cassette. It should be understood that the console may use other methods to actively detect or passively receive information from the mounted cassette regarding its functionality.

Figure 9A:
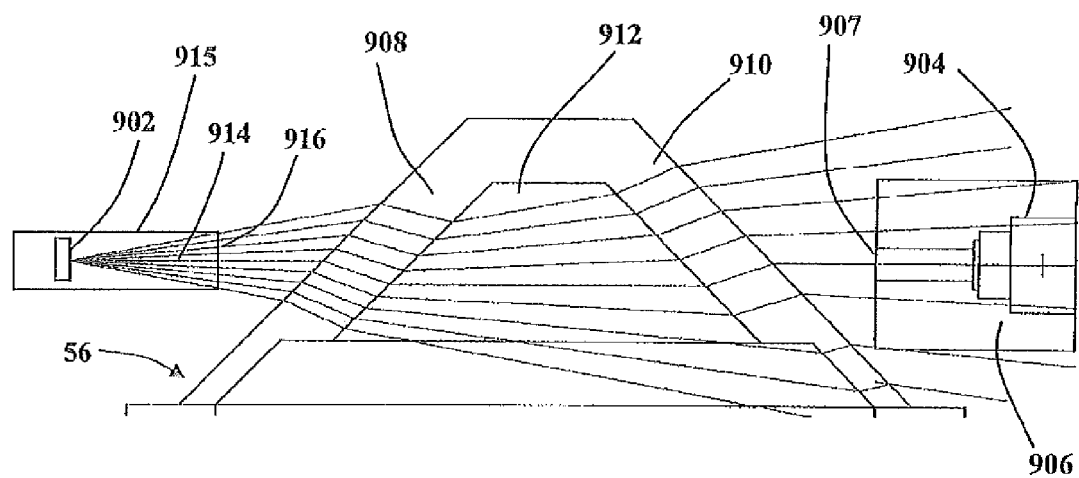
Figure 9B:
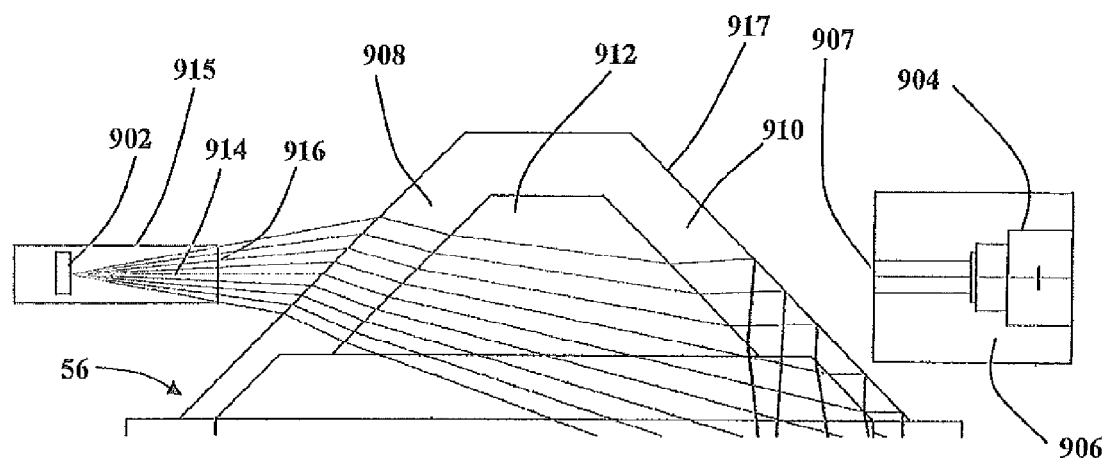

One embodiment of the invention is illustrated by the simulation shown in FIGS. 9(a) and 9(b), both of which show an emitter 902, for example a light-emitting or infrared-emitting diode, and a light detector or sensor 904 within a housing 906 with an entrance aperture 907. As used herein, the terms "light" will generally refer to electromagnetic radiation, preferably electromagnetic radiation in the infrared, visible, and ultraviolet wavebands. A section through holding tank 56 includes a first wall 908 and a second wall 910 with at least a volume portion 912 of the tank 56 disposed therebetween. In the illustrated embodiment, the volume portion 912 is generally disposed about a horizontal plane and may a substantially constant vertical thickness, although other shapes and orientations are possible. The first and second walls 908, 910 and the volume portion 912 are generally disposed between the light emitter 902 and the light detector 904.

Embodiments of the invention may comprise a single emitter/detector pair and associated volume portion, as illustrated in FIGS. 9(a) and 9(b). In other embodiments, a plurality of emitter/detector pairs and volume portions may be located at a plurality of different vertical heights along the holding tank 56, with each height generally corresponding to a different volume portion (although there may be some overlap between some of the volume portions). In one embodiment, detection system comprises three emitter/detector pairs, with the heights of each pair corresponding to fill quantities at which the drain pump should be turned on, at which the drain pump should be turned off, and at which an emergency shutdown of the system is appropriate. In such embodiments, each of emitters may be sequentially turned on and then off in order to preclude the possibility of cross-talk between the plurality of detectors. Other devices and means may additionally or alternatively be used to mitigate or preclude cross-talk between detectors, including, but not limited to, the use of different color emitters or detector sensitivities, the use of polarization, and the like.

In FIG. 9(a), rays 914 are shown for a photo-diode emitter 902 having a full divergence angle of about 20 degrees. Rays 19 generally indicate a locus of optical path of the light from light emitter 902. It will be appreciated that the emitter 902 may produce additional light outside of the rays 914 shown in FIG. 9(a), but that additional light is of sufficiently low intensity or power as to not affect the operation or function of sensor 904. In the illustrated embodiment, an emitter housing 915 includes an aperture 916 that may be used to limit the full divergence angle to a predetermined limit (e.g., about 20 degrees in the illustrated embodiment).

The first and second walls 908, 910 in FIGS. 9(a), 9(b) are at an angle of 90° to one another; however, other angular relationships between the first and second walls 908, 910 are possible. The aperture 916 may be configured to confine the light beam to keep it incident within the volume portion 912, with the exemplary emitter 902 preferably generating visible or infrared light. The propagation of the rays in FIG. 9(a) is shown for a condition in which there is no fluid present in the relevant portion for volume portion 912 in holding tank 56. Under these conditions, the central rays are essentially undeflected. The undeflected central ray from tank 56 enters housing 906 through detector aperture, proceeds straight down a bore of the housing and onto detector 904.

In FIG. 9(b), the system is shown with fluid being present in volume portion 912. The change in refractive index due to the presence of surgical fluid within the volume portion 912 results in most of the rays being totally internally reflected at the wall/air interface 917 near detector 904. The remaining rays are refracted and redirected so that they do not impinge upon the director housing 906, or at least do not travel down the bore to detector 904. The detector aperture in front of the sensor 904 reduces the amount of external stray or ambient light sensed by the sensor. Thus, when fluid is not present, the detector outputs a signal based on the presence of light from the emitter. However, when fluid is present, no light, or at least a lesser amount of light, from the emitter is received by the detector and the output is accordingly affected.

In some embodiments, the system 10 includes a threshold level that is selected such that a first output is generated when an amount of light from the emitter 902 entering the sensor 904 is below the threshold level, and a second output is generated when the amount of light from the emitter 902 entering the detector is equal to or above the threshold level. In some embodiments, the first output indicates that fluid is present in the volume portion 912 and the second output indicates that fluid is not present in the volume portion 912.

Alternatively, the emitter 902, detector 904, first wall 908, and second wall 910 may be configured such that the first output indicates that fluid is not present in the volume portion 912 and the second output indicates that fluid is present in the volume portion 912.

The spacing between the emitter/detector, and the diameter and location of the apertures 907, 916 may be selected to help provide a predetermined relationship between the first output and the second output. In some embodiments, the distance between the emitter/detector is between about 0.5 inches and about 1.0 inches, preferably about 0.8 inches. The diameter of the either or both of the apertures 907, 916 may be between about 0.025 and about 0.10 inches, preferably about 0.05 inches. In such embodiments, at least one of the apertures 907, 916 may be disposed in front of the detector 904 or emitter 902, respectively, by an amount that is between about 0.05 inches and about 0.2 inches, preferably about 0.10 inches. In certain embodiments, the ratio of the diameter of at least one of the apertures 907, 916 to the distance from the detector 904 and/or emitter 902, respectively, is selected to provide a desired threshold level between the first output and the second output.

Figure 10A:
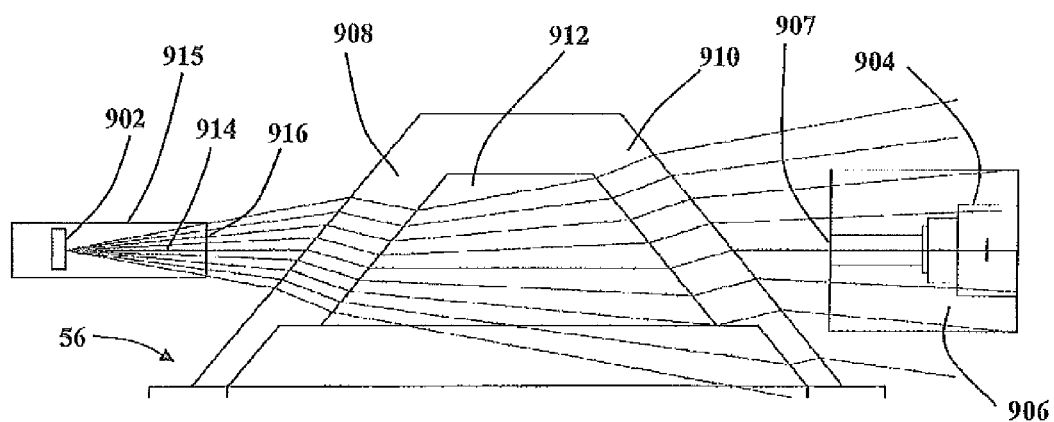
FIGS. 10(a) and 10(b) illustrate an alternative embodiment of a surgical fluid detection system similar to that of FIGS. 9(a) and 9(b).
Figure 10B:
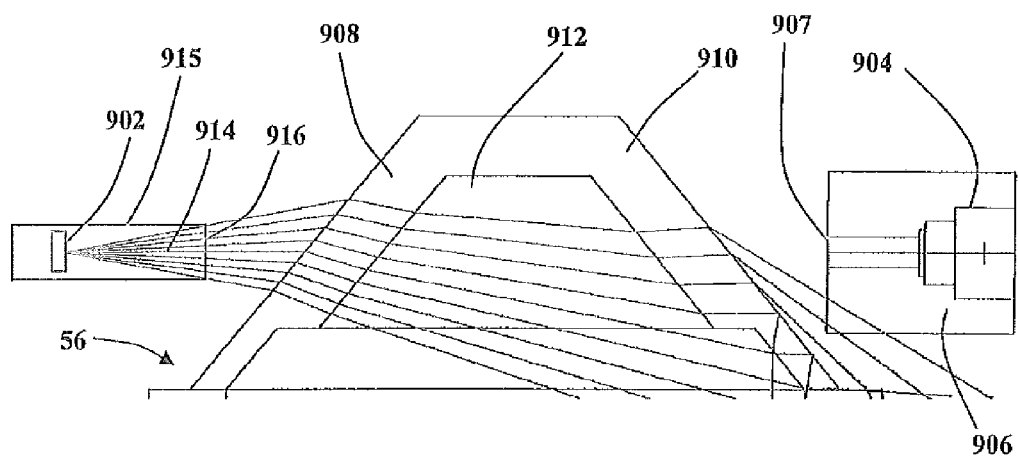

The embodiment of FIGS. 10(*a*) and 10(*b*) is similar to that of FIGS. 9(*a*) and 9(*b*), respectively. However, in this embodiment, walls 908, 910 of holding tank 56 are set at an angle of 80° to one another. When fluid is present (as in FIG. 10(*b*)), some of the rays are not internally reflected, since the incidence angle is less than that under the conditions shown in FIG. 9(*b*). However, even the rays that are not reflected back into tank 56 are diverted sufficiently to prevent those rays from impinging onto the recessed detector 904 within housing 906.

While exemplary embodiments of the surgical fluid detection system are described above, a variety of alternative arrangements may also be employed. For example, the refractive index of the wall material and angles of the walls where the beam enters and exits the tank may be altered, the spacing between the two walls may be adjusted depending on the characteristics of the light source (for example, the divergence angle and the like), depending on the characteristics of the detector, or depending on other system parameters such as ambient light, and the like. The walls themselves need not have parallel faces, but could (for example) each comprise wedges or prisms of small-angled flat walls, or other shapes (such as curved walls), if the detector is positioned appropriately. Alternative systems may operate in a manner substantially opposite to that of FIGS. 9(*a*)/(*b*) and 10(*a*)/(*b*), so that the system is configured with the detector not receiving light from the emitter when fluid is absent, but where the detector does receive light when fluid is present. One such system might employ the arrangement of FIG. 10(*a*) and 10(*b*), but with the housing 906 and detector 904 repositioned and reconfigured so as to receive the light refracted at a significant angle out of the second wall 910. A variety of structures of the console may be used to support emitter 902, light detector 904, and the like.

While the exemplary embodiments have been described in some detail for clarity of understanding and by way of example, a variety of changes, modifications, and adaptations will be obvious to those of skill in the art. Hence, the scope of the present invention is limited solely by the appended claims.

What is claimed is:

1. A surgical system comprising:
    a fluid detector system comprising a first emitter and a first signal receiver and a second emitter and a second signal receiver, wherein the first emitter is configured to emit a first color and the second emitter is configured to emit a second color, or the first emitter and first signal receiver are configured to employ light having a first polarization and the second emitter and second signal receiver are configured to employ light having a second polarization; and
    a cassette including a fluid container having a first wall and a second wall with a volume portion therebetween;
    the system configured to produce a first signal and a second signal when a light beam transmits through the first wall, the volume portion, the second wall, and into the first or second signal receiver;
    the system configured to produce a second signal when the second wall directs the light beam away from the first or second signal receiver by refraction and/or reflection;
    wherein the first emitter and first signal receiver are disposed at a first vertical height relative to the fluid container, and the second emitter and second signal receiver are disposed at a second vertical height, the second vertical height below the first vertical height to detect differing quantities of fluid in the fluid container.

2. The surgical cassette of claim 1, wherein the first and second emitters are configured to produce radiation in the infrared, visible, and/or ultraviolet wavebands.

3. The surgical system of claim 1, wherein the first and/or second emitter directs the light along a light path, wherein the first wall is at a first angle relative to the light path, and wherein the second wall is at a second angle relative to the first wall, and wherein the container is configured so that when no surgical fluid is disposed in the volume portion the light is refracted from the first wall into the volume portion and proceeds through the second wall and to the first and/or second receiver.

4. The surgical system of claim 3, wherein the light path from the first wall proceeds, when the surgical fluid is disposed in the volume portion, away from the first and/or second signal receiver so that a reduction of the light at the first and/or second signal receiver defines the second signal.

5. The surgical system of claim 4, wherein the light from the first wall into the surgical fluid proceeds along the path to the second wall at a sufficient angle relative to the second wall that the light is reflected by a surface of the second wall.

6. The surgical system of claim 3, wherein the first wall has first and second parallel surfaces so that the path of the light refracted into air in the volume portion is parallel to the path of the light from the first and/or second emitter, wherein the first wall is at a first oblique angle relative to the path from the first emitter, and wherein the second wall has first and second parallel surfaces and is at a second oblique angle relative to the path of the light through the air, the second angle complementary to the first angle so that the path of the light from the second wall is substantially coaxial with the path of light toward the first wall when no surgical fluid is in the volume.

7. The surgical system of claim 2, wherein the second signal corresponds to a condition in which the volume portion contains fluid and the first signal correspond to a condition in which the fluid volume contains only a gas.

8. A surgical cassette for use with an eye treatment system, the eye treatment system including a fluid detector system and a fluid aspiration drive system, wherein the fluid detector system comprises a first emitter and a first signal receiver and a second emitter and a second signal receiver, wherein the first emitter is configured to emit a first color and the second emitter is configured to emit a second color, or the first emitter and first signal receiver are configured to employ light having a first polarization and the second emitter and second signal receiver are configured to employ light having a second polarization, a fluid aspiration drive system, and a cassette frame configured to interchangeably receive a single mode cassette and a dual mode cassette, the cassette comprising:
- a surgical fluid aspiration system including a fluid container having a first wall and a second wall with a volume portion therebetween, the first and second walls configured so that when the cassette is mounted in the eye treatment system and light from the first or second emitter is directed to the first wall:
- the light defines a first signal at the first signal receiver when the volume portion is filled with surgical fluid; and
- the light defines a second signal at the second signal receiver when no surgical fluid is disposed in the volume portion;
- wherein the first emitter and first signal receiver are disposed at a first vertical height relative to the fluid container, and the second emitter and second signal receiver are disposed at a second vertical height, the second vertical height below the first vertical height to detect differing quantities of fluid in the fluid container.

9. An eye treatment method comprising:
aspirating surgical fluid from an eye;
holding aspirated surgical fluid in a fluid container having a first wall, a second wall, and a volume portion therebetween;
providing a fluid detector system comprising a first emitter and a first signal receiver and a second emitter and a second signal receiver, wherein the first emitter is configured to emit a first color and the second emitter is configured to emit a second color, or the first emitter and first signal receiver are configured to employ light having a first polarization and the second emitter and second signal receiver are configured to employ light having a second polarization;
controlling the amount of surgical fluid in the fluid container in response to first and second signals,
generating the first signal by transmitting a light beam through the first wall, the volume portion, the second wall, and into the first or second signal receiver; and
generating the second signal by directing the light beam away from the first or second signal receiver by refraction and/or reflection of the light beam by the second wall;
wherein the first emitter and first signal receiver are disposed at a first vertical height relative to the fluid container, and the second emitter and second signal receiver are disposed at a second vertical height, the second vertical height below the first vertical height to detect differing quantities of fluid in the fluid container.

10. The method of claim 9, wherein the first and second emitters are configured to produce radiation in the infrared, visible, and/or ultraviolet wavebands.

11. The surgical system of claim 1, wherein the dual mode cassette comprises components for a displacement-based pump and components for a vacuum-based pump.

12. The surgical system of claim 1, wherein the dual mode cassette is configured to aspirate fluid by a displacement-based pump or a vacuum-based pump.

13. The surgical system of claim 12, wherein the displacement-based pump is a peristaltic pump and the vacuum-based pump is a Venturi pump.

14. The method of claim 9, wherein the dual mode cassette comprises components for a displacement-based pump and components for a vacuum-based pump.

15. The method of claim 9, wherein the dual mode cassette is configured to aspirate fluid by a displacement-based pump or a vacuum-based pump.

16. The method of claim 15, wherein the displacement-based pump is a peristaltic pump and the vacuum-based pump is a Venturi pump.

17. The surgical system of claim 1, wherein the dual mode cassette comprises components for at least two displacement-based pumps and components for a vacuum-based pump.

18. The surgical system of claim 8, wherein the dual mode cassette comprises components for at least two displacement-based pumps and components for a vacuum-based pump.

19. The surgical system of claim 9, wherein the dual mode cassette comprises components for at least two displacement-based pumps and components for a vacuum-based pump.

* * * * *